US00PP12984P2

(12) United States Plant Patent
Jepsen

(10) Patent No.: US PP12,984 P2
(45) Date of Patent: Sep. 17, 2002

(54) KALANCHOE PLANT NAMED 'JEPMONI'

(75) Inventor: Knud Jepsen, Hinnerup (DK)

(73) Assignee: Knud Jepsen A/S, Hinnercup (DK)

( * ) Notice: Subject to any disclaimer, the term of this patent is extended or adjusted under 35 U.S.C. 154(b) by 89 days.

(21) Appl. No.: 09/822,002

(22) Filed: Mar. 31, 2001

(51) Int. Cl.[7] ..... A01H 5/00

(52) U.S. Cl. ..... Plt./341
(58) Field of Search ..... Plt./341

*Primary Examiner*—Bruce R. Campell
*Assistant Examiner*—Michelle Kizilkaya
(74) *Attorney, Agent, or Firm*—C. A. Whealy

(57) ABSTRACT

A distinct cultivar of Kalanchoe plant named 'Jepmoni', characterized by its numerous very dark red flowers; upright and compact plant habit; dark green leaves; and excellent postproduction longevity.

2 Drawing Sheets

BACKGROUND OF THE INVENTION

The present invention relates to a new and distinct cultivar of Kalanchoe plant, botanically known as *Kalanchoe blossfeldiana,* and hereinafter referred to by the name 'Jepmoni'.

The new Kalanchoe is a product of a planned breeding program conducted by the Inventor in Hinnerup, Denmark. The objective of the breeding program was to create new freely-flowering Kalanchoe cultivars with compact plant habit and excellent postproduction longevity.

The new Kalanchoe is a naturally-occurring whole plant mutation of the *Kalanchoe blossfeldiana* cultivar Juliana, disclosed in U.S. Plant Pat. No. 10,228. The cultivar Jepmoni was discovered and selected by the Inventor as a flowering plant within a population of plants of the ciltivar Juliana in a controlled environment in Hinnerup, Denmark.

Asexual reproduction of the new Kalanchoe by terminal cuttings taken at Hinnerup, Denmark, by the Inventor, has shown that the unique features of this new Kalanchoe are stable and reproduced true to type in successive generations.

BRIEF SUMMARY OF THE INVENTION

The cultivar Jepmoni has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Jepmoni'. These characteristics in combination distinguish 'Jepmoni' as a new and distinct cultivar:

1. Very dark red flowers.
2. Upright and compact plant habit.
3. Dark green leaves.
4. Excellent postproduction longevity.

Plants of the new Kalanchoe are most similar to plants of the cultivar Juliana and differ primarily from plants of the cultivar Juliana in flower color.

BRIEF DESCRIPTION OF THE PHOTOGRAPHS

The accompanying colored photographs illustrate the overall appearance of the new Kalanchoe, showing the colors as true as it is reasonably possible to obtain in colored reproductions of this type. Colors in the photographs may differ slightly from the color values cited in the detailed botanical description which accurately describe the colors of the new Kalanchoe. The photographs were taken under diffuse natural light conditions on an overcast day with electronic flash at approximately noon in Hinnerup, Denmark.

The photograph on the first sheet comprises a side perspective view of a typical potted plant of 'Jepmoni'.

The photograph at the top of the second sheet comprises a top perspective view of a typical potted plant of 'Jepmoni' showing the flowers and foliage.

The photograph at the bottom of the second sheet is a close-up view of the following: side and top perspective views of a typical flowering cyme and top perspective views of immature and fully expanded floral leaves of 'Jepmoni'.

DETAILED BOTANICAL DESCRIPTION

In the following description, color references are made to The Royal Horticultural Society Colour Chart except where general terms of ordinary dictionary significance are used. Plants used in the photographs and for the following observations and measurements were grown in Hinnerup, Denmark, under commercial practice in a glass-covered greenhouse for about 10 weeks after the start of short day/long night photoperiodic treatment with average temperatures of 20° C. Plants used in the description and photographs were not pinched. Unless otherwise specified, the leaf description represents leaves from a vegetative plant.

Botanical classification: *Kalanchoe blossfeldiana* cultivar Jepmoni.

Parentage: Naturally-occurring whole plant mutation of *Kalanchoe blossfeldiana* cultivar Juliana, disclosed in U.S. Plant Pat. No. 10,228.

Propagation:

*Type cutting.*—Terminal cuttings.

*Time to initiate roots.*—About 12 days.

*Root description.*—Numerous, fine, fibrous, and well-branched.

Plant description:

*Form.*—Upright and compact plant habit with numerous compound cymes; freely flowering. Actual plant shape will depend on whether or not plants are pinched (apical terminals removed). Finished plant size is appropriate for one plant per 9 to 10-cm container or three plants per 13-cm container.

*Branching habit*.—Freely branching. Pinching (removal of terminal apex) is not required but will enhance lateral branch development.

*Plant height at flowering*.—About 24 cm.

*Plant diameter at flowering*.—About 20 cm.

*Foliage description*.—Leaves simple, opposite, generally symmetrical. Size: Leaf size is reduced after floral induction. Vegetative plants: Length: About 11 cm. Width: About 9 cm. Reproductive plants: Length: About 7 cm. Width: About 4 cm. Shape: Oval. Apex: Obtuse. Base: Obtuse. Margin: Crenate; undulate. Aspect: Slightly concave. Texture: Leathery, glabrous, succulent, rugose. Color: Young foliage, upper surface: 137A, glossy. Young foliage, lower surface: 137C. Mature foliage, upper surface: 147A, glossy. Mature foliage, lower surface: 147B.

Flower description:

*Flower type and habit*.—Single flowers arranged in compound dichasial cymes that arise from leaf axils. Upright flowering stems. Freely flowering. Flowers persistent.

*Natural flowering season*.—Late autumn/winter/early spring; flower initiation and development can be induced under short day/long night conditions.

*Time to flower*.—In the summer with 20° C. growing temperatures, about 9 weeks of short day/long night conditions are required to produce flowering plants. During the winter with supplemental lighting and 20° C. growing temperatures, about 10 weeks of short day/long night conditions are required to produce flowering plants. Time to flower is primarily dependent upon temperature and light intensity.

*Flower opening*.—First flower open is the terminal flower at the main axis and is followed by the opening of the terminal flowers of the side branches of the inflorescence. About 1 weeks after the first flower has opened, 50% of the remaining flowers are open.

*Post-production longevity*.—Plants of the new Kalanchoe maintain good leaf and flower substance for at least five weeks under interior environmental conditions.

*Flower diameter*.—About 1.7 cm.

*Quantity*.—Very freely flowering, at least 250 flowers per plant.

*Flower buds*.—Shape: Narrowly oblong. Length: About 1.5 cm. Width: About 3 mm. Color: 46A.

*Petals*.—Quantity: Four fused at base. Length: About 9 mm. Shape: Round obovate. Apex: Cuspidate. Margin: Entire. Texture: Glabrous, smooth and satiny. Color: Upper surface: 187A to 185A. Lower surface: 185B.

*Reproductive organs*.—Stamens: Stamen number: Eight. Anther shape: Slightly oblong. Filament color: Yellow green. Pollen color: Yellow. Pistils: Pistil number: Four. Style color: Green. Stigma shape: Round. Ovaries: Superior and four-celled. Ovary size: About 5 mm by 1 mm. Ovary color: Light green.

*Seed*.—Seed production has not been observed.

Disease resistance: Resistance to known Kalanchoe diseases has not been observed on plants of the new Kalanchoe grown under commercial greenhouse conditions.

It is claimed:

1. A new and distinct cultivar of Kalanchoe plant named 'Jepmoni', as illustrated and described.

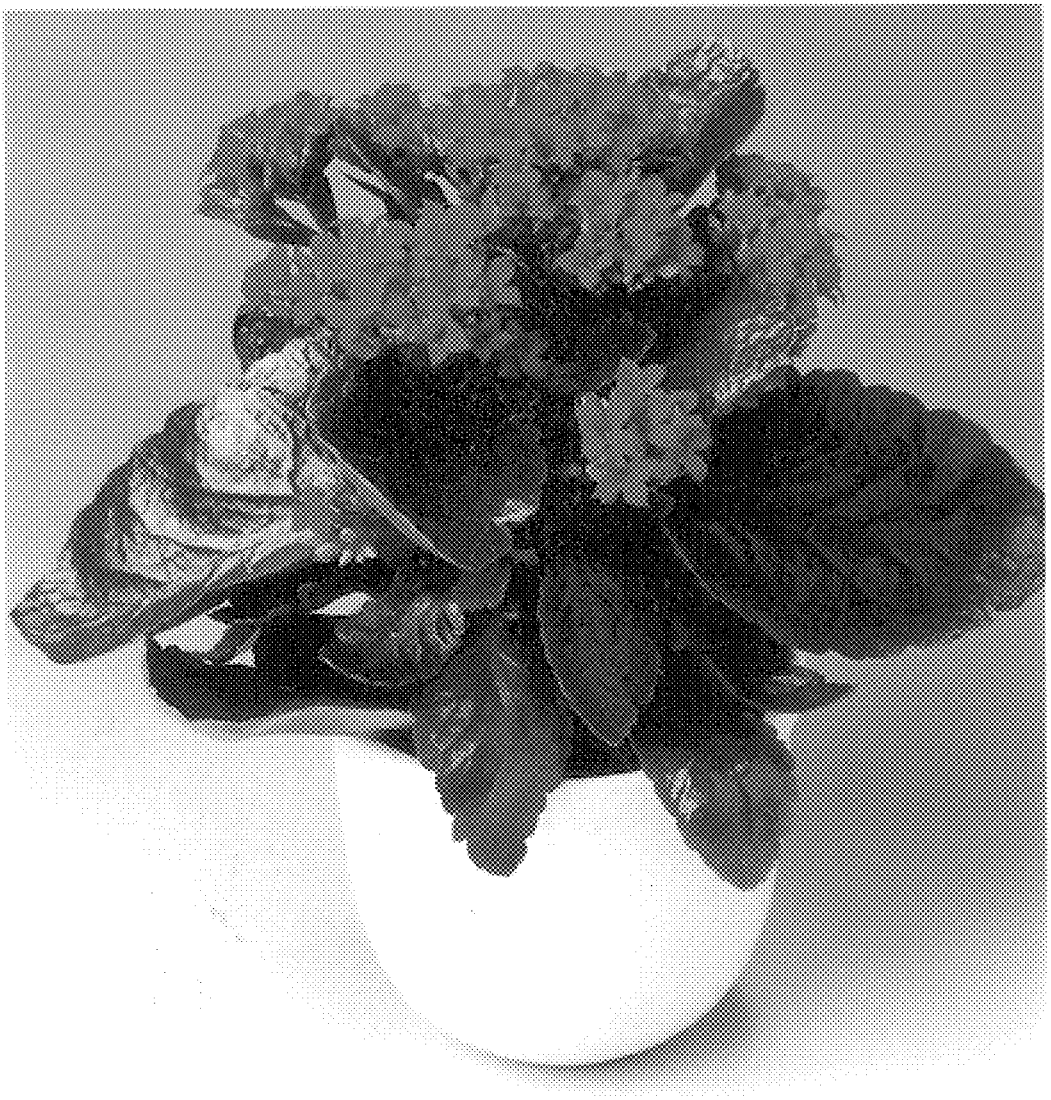

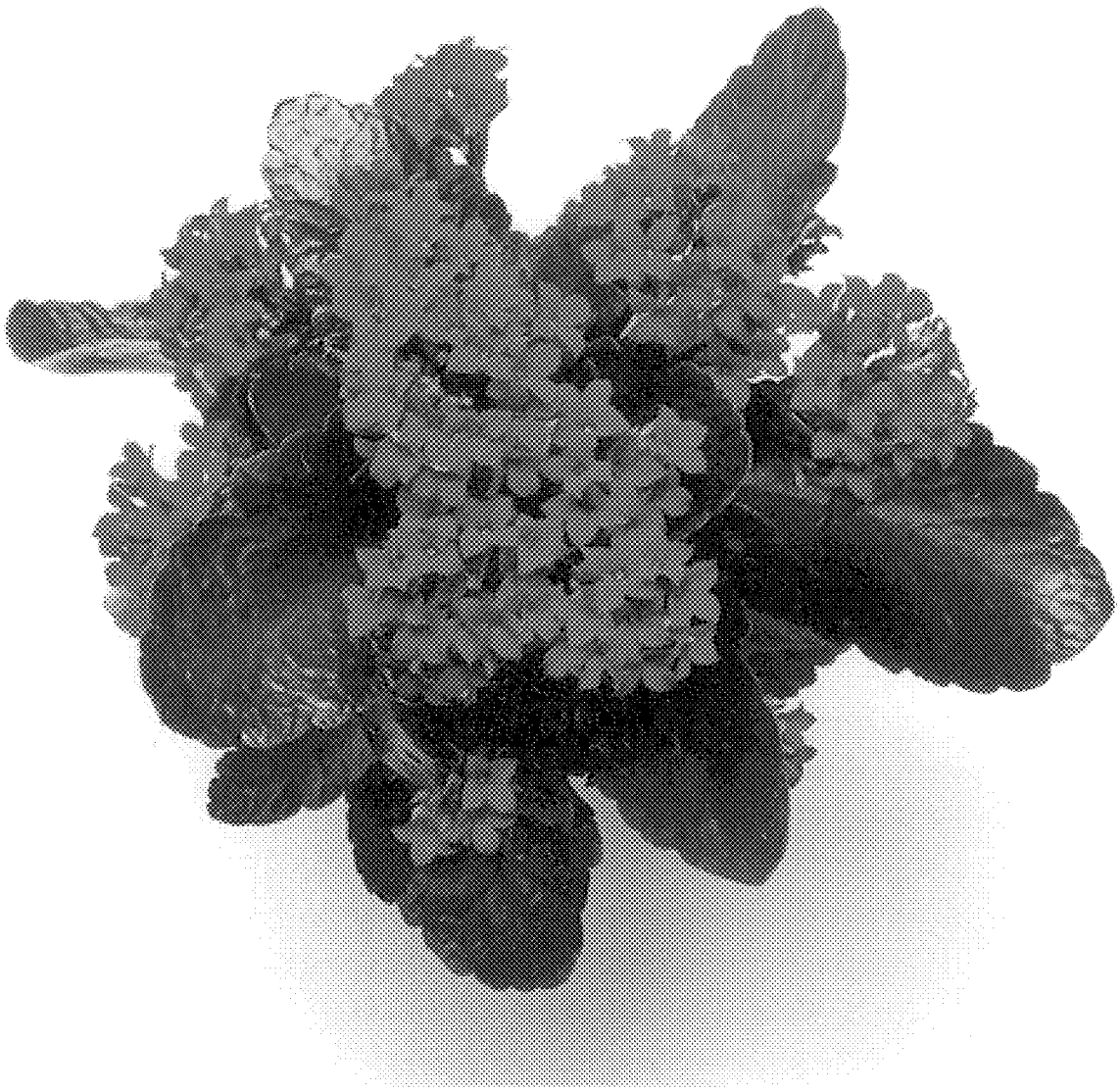
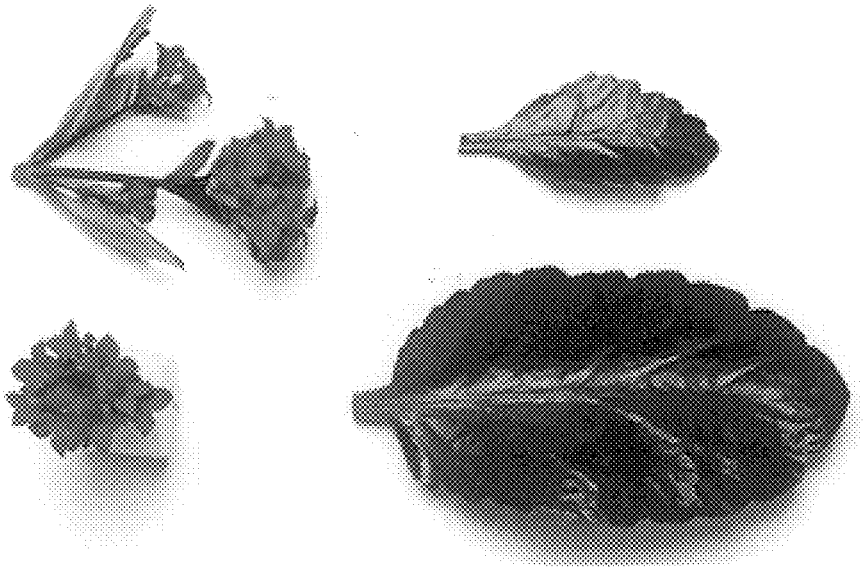

* * * * *